United States Patent [19]

Wang

[11] Patent Number: 5,013,805

[45] Date of Patent: May 7, 1991

[54] CURED RESIN PRODUCTS

[75] Inventor: Pen C. Wang, Houston, Tex.

[73] Assignee: Shell Oil Company, Houston, Tex.

[21] Appl. No.: 357,156

[22] Filed: May 26, 1989

Related U.S. Application Data

[63] Continuation-in-part of Ser. No. 324,870, Mar. 17, 1989, abandoned, which is a continuation-in-part of Ser. No. 245,433, Sep. 16, 1988, Pat. No. 4,847,388.

[51] Int. Cl.$^5$ ............................................. C08F 26/06
[52] U.S. Cl. .................................... 526/264; 528/323; 548/410
[58] Field of Search ....................... 526/264; 528/323; 548/410

[56] References Cited

U.S. PATENT DOCUMENTS

| | | | |
|---|---|---|---|
| 4,100,140 | 7/1978 | Zahir et al. | 526/90 |
| 4,468,524 | 8/1984 | Zahir et al. | 560/221 |
| 4,886,863 | 12/1989 | Wang | 526/262 |
| 4,921,931 | 5/1990 | Wang | 528/322 |

*Primary Examiner*—Joseph L. Schofer
*Assistant Examiner*—Alex H. Walker

[57] ABSTRACT

A novel class of cured products is derived from unsaturated polycylic ethers or esters comprising unsaturated ether or ester derivatives of a hydroxyaryl-substituted 1,6-diaza [4.4] spirodilactum having a hydroxyaryl substitute attached to each spiro ring nitrogen atom.

26 Claims, No Drawings

CURED RESIN PRODUCTS

RELATED APPLICATIONS

This application is a continuation-in-part of copending U.S. patent application Ser. No. 324,870, filed Mar. 17, 1989, now abandoned which is a continuation-in-part of copending U.S. patent application Ser. No. 245,433, filed Sept. 16, 1988, now U.S. Pat. No. 4,847,388.

FIELD OF THE INVENTION

This invention relates to a novel class of unsaturated ether or ester derivatives of spirodilactams having hydroxyaryl substituents on the spiro ring nitrogen atoms. More particularly, the invention relates to certain cured products derived from unsaturated ether or ester derivatives of a 1,6-diaza [4.4] spirodilactam having hydroxyaryl substituents in the 1- and 6- positions.

BACKGROUND OF THE INVENTION

Unsaturated ether or ester derivatives of polyhydric phenols are well known as a class of compounds that can be cured or crosslinked to produce insoluble products which exhibit good solvent resistance and mechanical properties as well as high heat distortion temperatures. Such unsaturated ethers are crosslinked by reaction with catalytic or stoichiometric curing agents, i.e., polyfunctional curing agents, to produce tough, heat resistant products which are processed by conventional methods into sheets, laminates with fiber glass or other reinforcements, or shaped articles and the crosslinked products are also useful in adhesive formulations. Certain of the unsaturated ethers cure into such products merely upon the application of heat without the necessity of a curing agent. Such materials are termed self-curing.

As indicated, much of the technology is broadly conventional. The disclosure of Zahir et al, U.S. Pat. No. 4,100,140, is illustrative. The compound 2,2-bis(4-hydroxyphenl)propane, also known as bisphenol A or BPA, is converted to the sodium salt and reacted with allyl chloride to produce the allyl ether of BPA, i.e., 2,2-bis(4-allyloxyphenyl)propane. The diallyl ether is converted to the diallyl-substituted BPA which is cured, but the diallyl ether is also curable without rearrangement. Curing takes place, for example, by reacting the diallyl ether with an imide-containing curing agent.

Other types of unsaturated derivatives of polyhydric phenols which are cured by such conventional techniques include unsaturated ester derivatives such as the acrylate and methacrylate esters of polyhydric phenols described by Zahir et al, U.S. Pat. No. 4,468,524.

On some occasions, the cured products which provide the more desirable properties, particularly in high temperature applications, are produced from unsaturated derivatives of aromatic phenolic compounds wherein some or all of the rings share common atoms with other rings of a polycyclic structure. It would be of advantage to provide a novel class of unsaturated derivatives of phenolic compounds having a plurality of rings within the molecular structure. Such unsaturated derivatives cure, with or without added curing agents, upon application of heat.

SUMMARY OF THE INVENTION

The present invention relates to a novel class of cured products produced from unsaturated derivatives of hydroxyaryl-substituted [4.4] spirodilactam compounds. More particularly, the invention relates to cured derivatives of unsaturated ether and ester derivatives of a 1,6-diazaspiro[4.4]nonane-2,7-dione compound having hydroxyaryl substituents on the ring nitrogen atoms of the spirodilactam ring system.

DESCRIPTION OF THE INVENTION

The novel cured products of the invention are produced from unsaturated ether or ester derivatives of hydroxyaryl-substituted 1,6-diazaspiro[4.4]nonane-2,7-dione having the hydroxyaryl substituents on the spiro ring nitrogen atoms and optionally having acyclic or cyclic substituents in the 3-, 4-, 8- and 9- positions of the spiro ring system. One class of such spirodilactams is represented by the formula

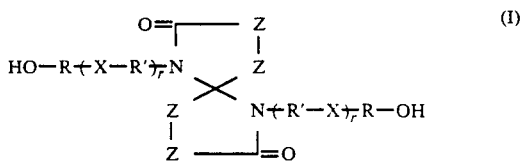

wherein Z independently is

in which Z' independently is hydrogen, lower alkyl of up to 4 carbon atoms, preferably methyl, halogen, preferably the lower halogens fluoro or chloro, or aryl, preferably phenyl, or Z is such that the two adjacent Z groups, taken together form a ring system Z" of from 5 to 7 ring atoms, up to two of which are heteroatoms selected from nitrogen atoms, oxygen atoms or sulfur atoms with the remainder of the ring atoms being carbon atoms, there being up to 15 carbon atoms in each Z", two of which connect the two carbon atoms connected by the adjacent Z groups. In the above formula I, R independently is aromatic of up to 15 carbon atoms and up to 2 aromatic rings, inclusive, R' is R or an aliphatic group of up to 10 carbon atoms inclusive. Each of R and R' is hydrocarbyl, i.e., contains only atoms of carbon and hydrogen, or is substituted-hydrocarbyl containing additional atoms in the form of inert substituents such as halogen, preferably the middle halogens chlorine or bromine. The term r in the above formula I independently is 0 or 1 and X is a direct valence bond, alkylene of up to 8 carbon atoms inclusive, oxy, thio, sulfonyl, carbonyl, dioxyphenylene, i.e.

2,2-di(oxyphenyl)propane, i.e.,

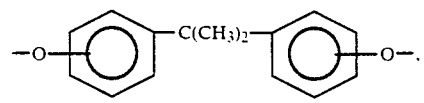

dioxyphenyl sulfone, i.e.,

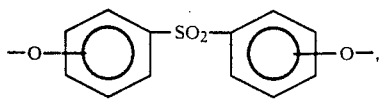

or dioxyphenylene, i.e.,

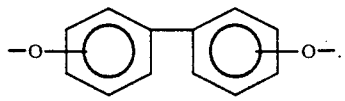

Spirodilactams of a considerable variety of structures are therefore suitably employed as a precursor of the unsaturated ether or ester derivatives of the invention. In the embodiment of the invention wherein the moieties of the above formula I are not part of a fused ring system and are therefor acyclic, i.e., Z is

the spirodilactam is illustrated by 1,6-di(4-hydroxyphenyl)-1,6-diazaspiro[4.4]nonane-2,7-dione, 1,6-di(3-hydroxy-4-chlorophenyl)-3,8-dimethyl-1,6-diazapiro[4.4]nonane-2,7-dione, 1,6-di(3-hydroxyphenyl)-3,8-diphenyl-1,6-diazaspiro[4.4]nonane-2,7-dione, 1,6-di[4-(4-hydroxybenzyl)phenyl]-1,6-diazaspiro[4.4]nonane-2,7-dione, 1,6-di(4-hydroxypehnyl)-3,3,4,4,8,8,9,9-octamethyl-1,6-diazaspiro[4.4]nonane-2,7-dione, 1,6-di[4-(4'-hydroxybiphenyl)]-3,3-dimethyl-1,6-diazaspiro[4.4]nonane-2,7-dione, 1,6-di[2-(4-hydroxyphenyl)propyl]1,6-diazaspiro[4.4]nonane-2,7-dione and 1,6-di[4-(4-hydroxyphenylisopropyl)-phenyl]-1,6-diazaspiro[4.4]nonane-2,7-dione. In the embodiment wherein adjacent Z moieties on each ring form a cyclic structure fused to the spiro ring system, illustrative spirodilactams include 1,6-di(4-hydroxyphenyl)-3,4,8,9-dibenzo-1,6-diazaspiro[4.4]nonane-2,7-dione, 1,6-di[4-(4-hydroxyphenyl)phenyl]-3,4,-8,9-dipyrido-1,6-diazaspiro[4.4]nonane-2,7-dione and 1,6-di[4-(4-hydroxyphenyloxy)phenyl]-3,4,8,9-di(cyclopentano)-1,6-diazaspiro[4.4]nonane-2,7-dione. Also suitable are those spirodilactams wherein one spiro ring has a fused ring substituent and the other spiro ring is free of fused ring substituents, e.g., 1,6-di(4-hydroxyphenyl)-3,4-benzo-8-methyl-1,6-diazaspiro[4.4]nonane-2,7-dione and 1,6-di[1-(4-hydroxynaphthyl)]3,4-cyclohexano-1,6-diazaspiro[4.4]nonane-2,7-dione.

In general, compounds of the above formula I wherein R and R' are aromatic and hydrocarbyl are preferred, especially such compounds wherein each r is 0. The class of 1,6-di(hydroxyphenyl) spirodilactams is particularly preferred. Within the spirodilactam portion of the molecule, spirodilactam rings which are substituted with hydrogen or methyl or fused with benzo rings are generally preferred, particularly the 1,6-diazospiro[4.4]nonane-2,7-diones.

The hydroxyaryl-substituted spirodilactams of the above formula I are compounds which are described and claimed as compositions of matter in U.S. Pat. No. 4,847,388.

The general method for the production of these spirodilactams, also described in this copending application and copending U.S. patent application Ser. No. 172,000, filed Mar. 23, 1988, now abandoned, and Ser. No. 172,052, filed Mar. 23, 1988, now abandoned, each of which is incorporated herein by reference, is by reaction of at least one hydroxy-containing primary amino compound and a spirodilactam precursor. In terms of the spirodilactam of the above formula I, the hydroxy-containing primary amino compound is represented by the formula

wherein R, R', X and r have the previously stated meanings. The spirodilactam precursor is a 4-oxoheptanedioic acid compound or a 1,6-dioxospiro[4.4]nonane-2,7-dione. In terms of the spirodilactam of the above formula I, the 4-oxoheptanedioic acid compound spirodilactam precursors are represented by the formula

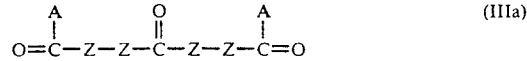

wherein Z has the previously stated meaning and A is hydroxy, lower alkoxy or halo, preferably middle halo. The spirodilactone spirodilactam precursor, in terms of the spirodilactams of formula I, is represented by the formula

wherein Z has the previously stated meaning.

Many of the acyclic 4-oxoheptanedioic acid compounds are known, but certain of the esters are also produced by the reaction of formaldehyde and unsaturated carboxylic acid esters by the process disclosed and claimed in U.S. Pat. No. 4,800,231. Interconversion of the acids, esters or acid halides of formula IIIa is by conventional methods. The production of 4-oxoheptanedioic acid compounds of formula IIIa which contain cyclic moieties is by the process of Cava et al, J. Am. Chem. Soc., 20,6022 (1955). The spirodilactones of formula IIIb are produced by the process of Pariza et al, Synthetic Communications, Vol. 13(3), pp. 243-254 (1983), or if the spirodilactones have additional fused rings by the process of U.S. Pat. No. 1,999,181.

The hydroxy-containing primary amino compound and the spirodilactam precursor react in a molar ratio of 2:1 although in practice reactant ratios from about 8:1 to about 1:1.5 are satisfactory. Reactant ratios of hydroxy-containing primary amino compound to spirodilactam precursor which are substantially stoichiometric are preferred. Reaction is conducted in a liquid phase solution in an inert reaction diluent such as an N-alkylamide, e.g., N,N-dimethylformamide, N,N-dimethylacetamide or N-methyl-2-pyrrolidone. Reaction takes place under reaction conditions at an elevated temperature, typically from about 80° C. to about 250° C., and at a reaction pressure sufficient to maintain the reaction mixture in a liquid phase, e.g., pressures up to about 20 atmospheres. Subsequent to reaction the spirodilactam product (of formula I) is recovered from the product mixture by conventional methods such as solvent removal, precipitation and chromatographic separation. Recovery of the spirodilactam product is not required, however, and particularly in cases where substantially stoichiometric quantities of reactants were employed the spirodilactam may be reacted further in situ to form derivatives such as the unsaturated ether or ester derivatives of the hydroxyaryl-substituted spirodilactams of the invention.

The unsaturated derivatives of the hydroxylaryl-substituted spirodilactams are ether or ester derivatives of the hydroxyaryl substituents derivatized at the hydroxyl group through ether or ester formation. The unsaturated moiety which becomes bound to the oxygen of the oxyaryl moiety (derived by loss of hydrogen from the hydroxyaryl moiety) is a group of up to 10 carbon atoms inclusive which contains carbon-carbon unsaturation located at least adjacent to the carbon atom of the unsaturated moiety which is bound to an oxyaryl residue of the hydroxyaryl substituents of the hydroxyaryl-substituted spirodilactam. Although unsaturated moieties of a number of types are useful in the ether or ester derivatives of the invention, the preferred unsaturated ether or ester moieties are selected from 2-alkenyl, 2-alkynyl, vinylarylmethyl and 2-alkenoyl. Illustrative alkenyl groups include allyl, methallyl and crotyl while alkynyl groups include propargyl and 2-octynyl. Vinylarylmethyl groups are exemplified by 4-styrylmethyl and 4-vinyl-2-methylbenzyl. The alkenoyl groups present when ester derivatives are desired include acrylyl, methacrylyl, 2,4-hexadienoyl and 2-hexenoyl. Preferred unsaturated moieties are allyl, propargyl and 4-vinylbenzyl in the case of ether derivatives and acrylyl and methacrylyl when ester derivatives are contemplated.

These preferred derivatives of the hydroxyaryl-substituted spirodilactams are represented by the formula

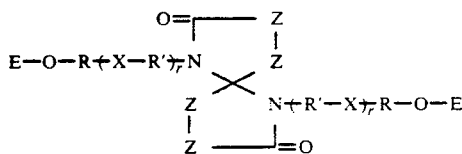

(IV)

wherein R, R', X, r and Z have the previously stated meanings and E independently is an unsaturated moiety of up to 10 carbon atoms inclusive containing carbon-carbon unsaturation at least adjacent to the carbon atom of E through which E is bound to the oxyaryl moiety. E is preferably allyl, propargyl, 4-styrylmethyl, acrylyl or methacrylyl.

These derivatives are typically produced by reacting a compound containing the desired ether or ester moiety with an alkali metal salt of the hydroxyaryl-substituted spirodilactam. Although lithium, sodium, potassium, rubidium and cesium salts of the hydroxyaryl-substituted spirodilactams are usefully employed in the production of the unsaturated ether derivatives of the invention, the use of a sodium salt or a potassium salt is preferred. In one modification, the alkali metal salt of the hydroxyaryl-substituted spirodilactam is produced by contacting the spirodilactam with a substantially stoichiometric quantity of alkali metal hydroxide, i.e., substantially 2 moles of alkali metal hydroxide for each mole of the spirodilactam. Sodium or potassium hydroxide is preferred. Reaction is conducted in the liquid phase in a suitable reaction solvent such as N,N-dimethylacetamide or N,N-dimethylformamide while removing the water present or formed by distillation, preferably azeotropic distillation employing a second solvent such as toluene or ethylbenzene with which water forms an azeotrope. The use of an alkali metal hydroxide is not specifically required and employment of an equivalent amount of alkali metal carbonate or bicarbonate is satisfactory. The alkali metal salt of the hydroxyaryl-substituted spirodilactam is isolated if desired by conventional procedures such as solvent removal but the salt is typically used in situ in the media of its production for reaction with the compound containing the unsaturated ether moiety.

The unsaturated moiety, E, is provided to the reaction with the alkali metal salt of the hydroxyaryl-substituted spirodilactam in the form of a halide or an alkoxide. The compound employed as the reactant which contains the unsaturated ether moiety is therefore represented by the formula $$E-G \qquad (V)$$

wherein E is the unsaturated ether or ester moiety as above defined and G is halo, preferably middle halogen chlorine or bromine, or lower alkoxy of up to 4 carbon atoms. When an ether derivative of the hydroxyaryl-substituted spirodilactam is desired the E moiety is preferably allyl, propargyl or 4-styrylmethyl and is generally provided as the halide. Allyl chloride, allyl bromide, propargyl bromide and p-vinylbenzyl chloride are illustrative. When an ester derivative of the hydroxyaryl-substituted spirodilactam is desired, the preferred acrylyl or methacrylyl moiety is typically provided as the alkoxide, i.e., as the acrylic or methacrylic ester, or as the halide, i.e., the acid halide. Methyl acrylate, methyl methacrylate, ethyl methacrylate, methacrylyl chloride or acrylyl bromide are illustrative of suitable sources of the unsaturated moiety for unsaturated ester derivatives.

The reaction of the alkali metal salt of the hydroxyaryl-substituted spriodilactam and the E-G compound is conducted in liquid phase solution in the presence of a reaction diluent. Preferred diluents are polar diluents in which the compounds undergoing are soluble, at least at reaction conditions. Suitable reaction diluents include N-alkylamides such as N,N-dimethylacetamide, N,N-dimethylformamide and N-methyl-2-pyrrolidone, phenols such as phenol and m-cresol and sulfur containing diluents such as sulfolane and dimethylsulfoxide. The compound which provides the unsaturated ether or ester moiety, i.e., the compound E-G, is utilized in a molar amount equal to or in excess over the alkali metal salt. Molar ratios from about 5:1 to about 1:1 are suitable. The stoichiometry of the reaction would suggest reaction of the E-G compound and the alkali metal salt in a 2:1 ratio. Molar ratios of from about 3:1 to about 1.5:1 are preferred.

Reaction is effected by charging the unsaturated moiety compound, the alkali metal salt of the hydroxyaryl-substituted spirodilactam and the reaction diluent to a suitable reactor and maintaining the reaction mixture under reaction conditions. Alternatively, the alkali metal salt is employed as produced in the media of its production and the E-G compound is added to the solution of the alkali metal salt if produced in a suitable reaction diluent.

Reaction to produce the unsaturated ether or ester derivatives of the hydroxyaryl-substituted spirodilactam is conducted over a range of reaction conditions, typically including a reaction temperature of from about −30° C. to about 200° C., preferably from about −10° C. to about 175° C. The higher portion of the temperature range is preferred for ether production while esters are more often formed in the lower portion of the temperature range. A suitable reaction pressure is one which will maintain the reaction mixture in the liquid phase. Such pressures are typically up to about 20 atmospheres but more often are from about 0.8 atmosphere to about 5 atmospheres. Reactant contact is maintained during reaction by conventional methods such as shaking or stirring and subsequent to reaction the desired ether or ester product is recovered by typical methods such as selective extraction, solvent removal or precipitation followed by filtration or decantation.

The ether and ester derivatives of the hydroxy-substituted spirodilactams find utility as thermosetting resins which are employed in the production of the cured or crosslinked products of the invention. These products are useful as surface coatings, in adhesive formulations and in fiber-reinforced composites wherein, for example, the fiber is glass or carbon. The cured products are also useful in the production of hollow objects as by filament winding and are employed as impregnating and casting resins. The processing of the cured products for these applications is by conventional methods.

The curing of the unsaturated ethers or esters is accomplished by conventional methods such as thermal curing, e.g., heating to a temperature above about 200° C., by photochemical excitation, e.g., as by exposure to high energy radiation, by catalyzed polymerization employing cationic or anionic catalysts or by reaction with a polyfunctional curing agent. Anionic polymerization uses alkali metal alkoxides, hydroxides or amides as the catalyst typical cationic polymerization catalysts are organic or inorganic acids or are Lewis acids. Such cationic catalysts include sulfuric acid, phosphonic acid, p-toluenesulfonic acid, boron trifluoride and tin tetrachloride. Catalytic catalysts are generally employed in a quantity of from about 0.05% by weight to about 5% by weight, based on total composition. In an alternate modification, the unsaturated ether or ester derivatives are cured by heating with a substantial amount, e.g., from about 20% by weight to about 50% by weight, based on total composition, of a polyfunctional curing agent.

In the present invention the preferred cured products are obtained by reacting the unsaturated ether or ester derivatives with a polyfunctional curing agent. Such curing agents are organic compounds having at least two substituents with multiple bonds between adjacent atoms. Such substituents are hydrocarbyl with multiple bonds between adjacent carbon atoms or are non-hydrocarbyl with multiple bonds between atoms at least one of which is not a carbon atom. Preferred polyfunctional curing agents have up to 30 carbon atoms inclusive and contain frunctional groups selected from alkenyl, alkynyl, styrylmethyl, cyanato or maleimido. Particularly preferred are the maleimido-substituted polyfunctional curing agents, especially di(4-maleimidophenyl)methane. This class of curing agents is described in greater detail by Zahir et al, U.S. Pat. No. 4,100,140. The other classes of polyfunctional curing agents are also well known in the art, and include such preferred curing agents as triallyl isocyanurate, di(4-cyanatophenyl)methane and 2,2-di(4-cyanatophenyl)propane. The invention is further illustrated by the following Illustrative Embodiments which should not be construed as limiting the invention.

ILLUSTRATIVE EMBODIMENT I

To a three liter three-necked flask was added a mixture of 202.8 g (0.6 mole) of 1,6-di(4-hydroxyphenyl)-1,6-diazaspiro[4.4]nonane-2,7-dione, 91.22 g (0.6 mole) of potassium carbonate, 200 ml of toluene and 1 liter of N,N-dimethylacetamide. The mixture was heated to 150°–160° C. and water removed by azeotropic distillation. When the water removal was complete, the temperature was lowered to 80°–90° C. and 200.2 g (1.66 mole) of allyl bromide in 200 ml of N,N-dimethylacetamide was added over the next 80 minutes. The reaction temperature was then raised for 12 hours and then the resulting mixture was cooled and filtered. The filtrate was concentrated and then poured slowly into a mixture of heaxane and ether. The precipitated product was recovered by filtration and dried in a vacuum oven at 80° C. The product had a melting point of 152°–155° C. and the nuclear magnetic resonance spectra were consistent with the formula 1,6-di(4-allyloxyphenyl)-1,6-diazaspiro[4.4]nonane-2,7-dione.

ILLUSTRATIVE EMBODIMENT II

The product of Illustrative Embodiment I was mixed with an equal portion by weight of bismaleimide, i.e., di(4-maleimidophenyl)methane. The resulting mixture was heated at 170° C. for 2 hours, at 210° C. for 2 hours and finally at 250° C. for 6 hours. The resulting cured product was insoluble in common solvents and had a glass transition temperature of 312° C.

ILLUSTRATIVE EMBODIMENT III

To a three liter three-necked flask was added a mixture of 135.2 g (0.4 mole) of 1,6-di(4-hydroxyphenyl)-1,6-diazaspiro[4.4]nonane-2,7-dione, 58.0 g (0.42 mole) of potassium carbonate, 500 ml of N,N-dimethylformamide and 200 ml of toluene. The mixture was heated to 150°–160° C. and the water was removed by azeotropic distillation. When the water removal was complete, the temperature was lowered to 80°–90° C. and 95.2 g (0.8 mole) of propargyl bromide in 100 ml of N,N-dimethylformamide was added over a 2.5 hour period. The reaction temperature was then raised to 100° C. and maintained at that temperature for 12 hours. The resulting solution was then cooled, filtered and reduced in volume upon a rotary evaporator. The concentrated solution was poured slowly into water to give a precipitated product which was recovered by filtration and dried in a vacuum oven at 80° C. The product had a melting point of 210°–216° C. and the nuclear magnetic resonance spectra were consistent with the structure 1,6-di(4-propargyloxyphenyl)-1,6-diazaspiro[4.4]nonane-2,7-dione.

This product was cured by heating for 12 hours at 210° C. The cured product had a glass transition temperature of 305° C.

ILLUSTRATIVE EMBODIMENT IV

To a two liter, 3-necked round-bottomed flask was added 135.2 g (0.4 mole) of 1,6-di(4-hydroxyphenyl)-1,6-diazaspiro[4.4]nonane-2,7-dione, 58.0 g (0.42 mole) of potassium carbonate, 200 ml of toluene and 250 ml of N,N-dimethylacetamide. The flask and contents were heated to 150°-160° C. and the water present or formed was removed by azeotropic distillation. When the water removal was complete, the temperature of the resulting mixture was lowered to 80°-90° C. and 152.6 g (0.84 mole) of vinylbenzyl chloride in 50 ml of N,N-dimethylacetamide were added over the next 30 minutes and the temperature was maintained for 12 hours. The resulting midxture was then cooled, filtered and poured into 3 liters of water. The insoluble porduct was removed by filtration, washed with water and dried. The product had a melting point of 153°-154° C. and the nuclear magnetic resonance spectra of the product were consistent with the structure 1,6-[4-(4-vinylbenzyl)oxyphenyl]-1,6-diazaspiro[4.4]nonane-2,7-dione.

ILLUSTRATIVE EMBODIMENT V

The vinylbenzyl ether of Illustrative Embodiment IV was heated at 200° C. and then at 220° C. for an additional 4 hours. The resulting cured product had a glass transition temperature of 273° C.

ILLUSTRATIVE EMBODIMENT VI

An equal mixture by weight of the vinylbenzyl ether of Illustrative Embodiment IV and di(4-maleimidophenyl)methane was melted at 150°-160° C. and then heated in an oven in a first stage to 200° C. for 2 hours and in a second stage at 220° C. for an additinoal 4 hours. The resulting cured product had a glass transition temperature in excess of 300° C.

ILLUSTRATIVE EMBODIMENT VII

An equal mixture by weight of the vinylbenzyl ether of Illustrative Embodiment IV and di(4-cyanatophenyl)methane was melted at 100°-120° C. The resulting mixture was heated in an oven in a first stage at 200° C. for 2 hours and in a second stage at 220° C. for an additional 4 hours. The resulting cured product had a glass transition temperature of 229° C.

ILLUSTRATIVE EMBODIMENT VIII

A mixture of 50 parts by weight of the vinylbenzyl ether of Illustrative Embodiment IV, 45 parts by weight of di(4-cyanatophenyl)-methane and 5 parts by weight of di(4-maleimidophenyl)methane was melted at 100°-120° C. The resulting mixture was then heated in an oven in a first stage at 200° C. for 2 hours and at 220° C. for an additional 4 hours. The resulting cured product had a glass transition temperature of 226° C.

ILLUSTRATIVE EMBODIMENT IX

An equal mixture by weight of the vinylbenzyl ether of Illustrative Embodiment IV and triallylisocyanurate was melted at 100°-120° C. The resulting mixture was heated in an oven in a first stage at 200° C. for 2 hours and then in a second stage at 220° C. for an additional 4 hours. The resulting cured product had a glass transition temperature of 205° C.

What is claimed is:

1. The crosslinked product obtained by heating an unsaturated ether or ester derivative of a hydroxyaryl-substituted spirodilactam, said spirodilactam having nitrogen atoms in the 1- and 6-positions of the spiro ring system and having a hydroxyaryl substituent on each spiro ring nitrogen atom, said derivatives being unsaturated moiety derivatives of the oxyaryl residue of each hydroxyaryl substituent, the unsaturated moiety of the ether or ester having up to 10 carbon atoms and carbon-carbon unsaturation at least adjacent to the carbon atom through which the unsaturated ether or ester moiety is bound to an oxyaryl residue of the hydroxyaryl substituent.

2. The product of claim 1 wherein the derivative is represented by the formula

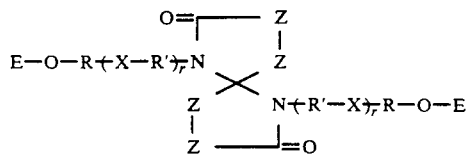

wherein Z independently is

in which Z' independently is hydrogen, lower alkyl, halogen or phenyl or Z is such that two adjacent Z groups taken together form a ring system Z" of from 5 to 7 atoms, up to two of which are heteroatoms selected from nitrogen, oxygen or sulfur, there being up to 15 carbon atoms in each Z", two of which connect the carbon atoms connected by the adjacent Z groups, R is aromatic of up to 15 carbon atoms and up to two aromatic rings, inclusive; R' is R or aliphatic of up to 10 carbon atoms inclusive; r is 0 or 1; X is a direct valence bond, alkylene of up to 8 carbon atoms inclusive, oxy, thio, sulfonyl, carbonyl, dioxyphenylene, 2,2-di(oxyphenyl)propane or dioxydiphenylene; and E independently is allyl, propargyl, 4-styrylmethyl, acrylyl or methacrylyl.

3. The product of claim 2 wherein each r is 0.

4. The product of claim 3 wherein Z is

5. The product of claim 4 wherein Z' is hydrogen.
6. The product of claim 4 wherein E is allyl.
7. The product of claim 4 wherein E is propargyl.
8. The product of claim 4 wherein E is 4-styrylmethyl.
9. The product of claim 2 wherein the heating is in the presence of a curing agent.
10. The product of claim 9 wherein the curing agent has at least two substituents having multiple bonds between adjacent carbon atoms.
11. The product of claim 10 wherein the substituents of the curing agent are alkenyl, alkynyl, styrylmethyl, cyanato or maleimido.
12. The product of claim 11 wherein each r is 0.
13. The product of claim 12 wherein each R is p-phenylene.
14. The product of claim 13 wherein Z is

15. The product of claim 14 wherein each Z' is hydrogen.

16. The product of claim 15 wherein E is allyl.

17. The product of claim 16 wherein the substituents of the curing agent are maleimido.

18. The product of claim 17 wherein the curing agent is di(4-maleimidophenyl)methane.

19. The product of claim 15 wherein E is 4-styrylmethyl.

20. The product of claim 19 wherein the substituents of the curing agent are maleimido.

21. The product of claim 20 wherein the curing agent is di(4-maleimidophenyl)methane.

22. The product of claim 19 wherein the curing agent is di(4-cyanatophenyl)methane.

23. The product of claim 19 wherein the curing agent is triallylisocyanurate.

24. The product of claim 13 wherein adjacent Z groups are Z''.

25. The product of claim 24 wherein Z'' is benzo.

26. The process of claim 25 wherein E is allyl.

* * * * *